(12) United States Patent
Marshall

(10) Patent No.: US 11,480,564 B2
(45) Date of Patent: Oct. 25, 2022

(54) KIT FOR THE DETECTION OF UREASE

(71) Applicant: Infagen (Hong Kong) Limited, Hong Kong (CN)

(72) Inventor: Barry Marshall, Shenton Park (AU)

(73) Assignee: Infagen (Hong Kong) Limited, Kowloon (HK)

( * ) Notice: Subject to any disclaimer, the term of this patent is extended or adjusted under 35 U.S.C. 154(b) by 326 days.

(21) Appl. No.: 15/778,952

(22) PCT Filed: Nov. 23, 2016

(86) PCT No.: PCT/AU2016/051142
§ 371 (c)(1),
(2) Date: May 24, 2018

(87) PCT Pub. No.: WO2017/088013
PCT Pub. Date: Jun. 1, 2017

(65) Prior Publication Data
US 2018/0348209 A1    Dec. 6, 2018

(30) Foreign Application Priority Data
Nov. 27, 2015   (AU) ................................ 2015904930

(51) Int. Cl.
*G01N 33/52* (2006.01)
*G01N 33/569* (2006.01)
(Continued)

(52) U.S. Cl.
CPC ............. *G01N 33/528* (2013.01); *C12Q 1/58* (2013.01); *G01N 33/62* (2013.01); *G01N 21/78* (2013.01);
(Continued)

(58) Field of Classification Search
CPC ...... C12Q 1/58; G01N 21/78; G01N 2800/06; G01N 33/528; G01N 33/56911; G01N 33/62
See application file for complete search history.

(56) References Cited

U.S. PATENT DOCUMENTS 5,439,801 A    8/1995  Jackson
6,241,687 B1   6/2001  Voegele et al.
(Continued)

FOREIGN PATENT DOCUMENTS

CN    201150547 Y    11/2008
EP        0112077     6/1984
(Continued)

OTHER PUBLICATIONS

International Search Report and Written Opinion dated Jan. 5, 2017 in International Application No. PCT/AU2016/051142, 17 pgs.
(Continued)

*Primary Examiner* — Lydia Edwards
(74) *Attorney, Agent, or Firm* — Fish & Richardson P.C.

(57) ABSTRACT

The present invention relates to a kit for the detection of urease and to a tool and a composition forming part of the kit. In particular, the present invention relates to a kit for the detection of urease which comprises a composition containing an indicator; a delivery tool arranged to deliver a tissue sample into contact with the composition; and urea carried on the delivery tool, whereby the urea is arranged to be delivered to the composition together with the tissue sample.

23 Claims, 6 Drawing Sheets

(51) Int. Cl.
  *G01N 33/62* (2006.01)
  *C12Q 1/58* (2006.01)
  *G01N 21/78* (2006.01)

(52) U.S. Cl.
  CPC .... *G01N 33/56911* (2013.01); *G01N 2800/06* (2013.01)

(56) References Cited

U.S. PATENT DOCUMENTS

| | | | |
|---|---|---|---|
| 8,216,832 | B2 | 7/2012 | Battrell et al. |
| 2003/0077684 | A1 | 4/2003 | Marshall et al. |
| 2008/0206889 | A1* | 8/2008 | Harris .............. G01N 33/54313 436/518 |
| 2010/0274155 | A1* | 10/2010 | Battrell .............. A61B 10/0096 600/572 |
| 2012/0094371 | A1 | 4/2012 | Ross et al. |
| 2012/0190589 | A1 | 7/2012 | Anderson et al. |

FOREIGN PATENT DOCUMENTS

| | | |
|---|---|---|
| PL | 215 889 | 8/2010 |
| WO | WO03/034061 | 4/2003 |

OTHER PUBLICATIONS

CN Office Action in Chinese Appln. No. 20168006947.9, dated Apr. 30, 2021, 20 pages (with English translation).

EP Extended European Search Report in European Appln. No. 16867446.3, dated Mar. 11, 2019, 7 pages.

PCT International Preliminary Report on Patentability in International Appln. No. PCT/AU2016/051142, dated Jul. 21, 2017, 5 pages.

* cited by examiner

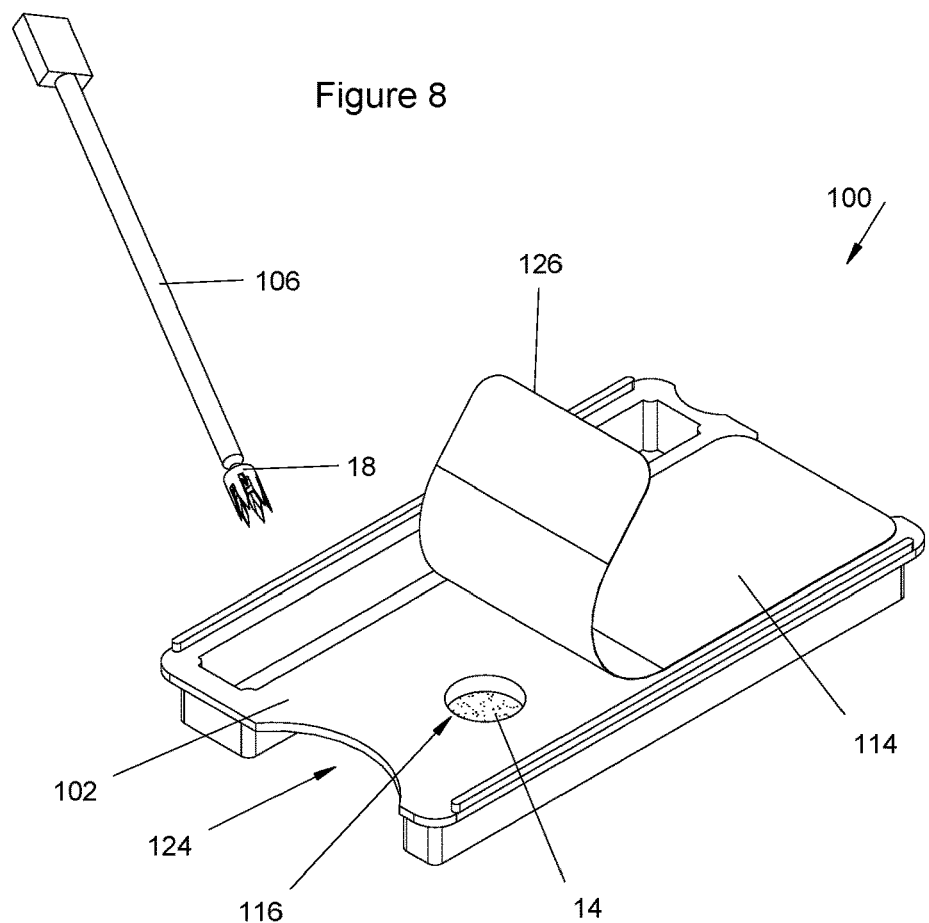
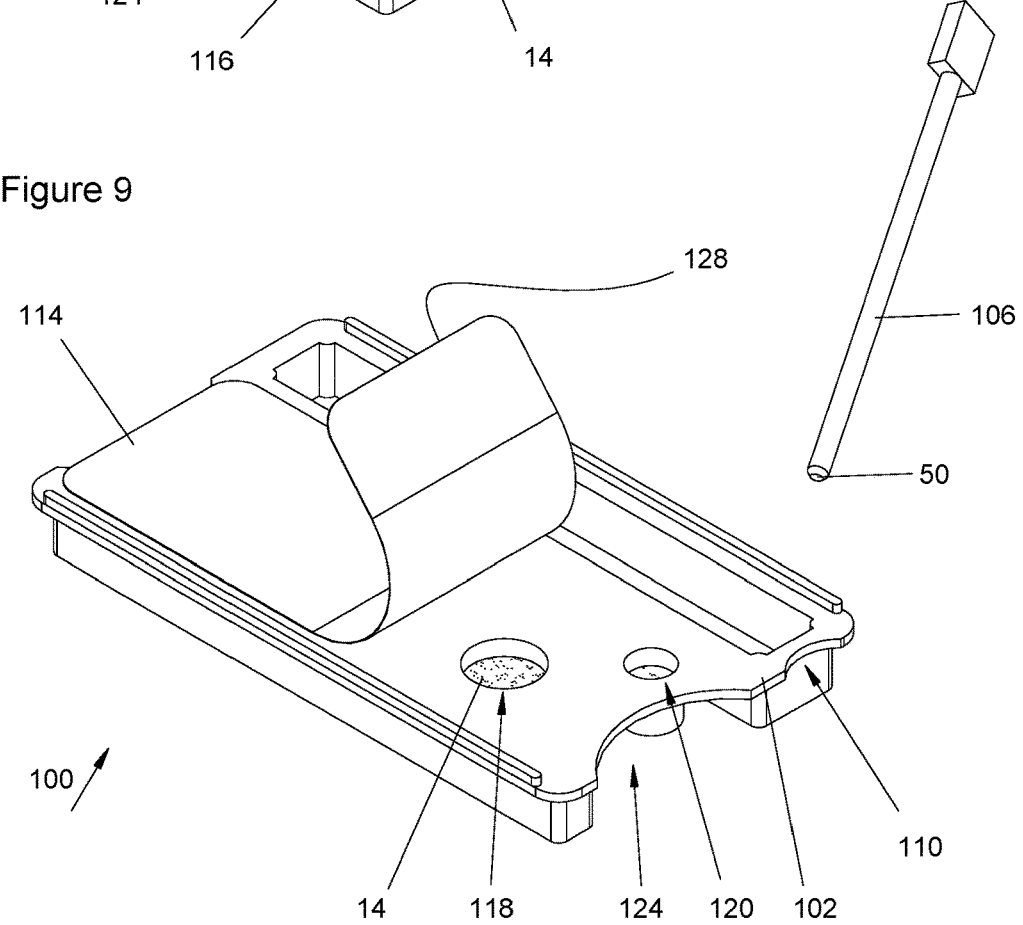

KIT FOR THE DETECTION OF UREASE

FIELD OF INVENTION

The present invention relates to a kit for the detection of urease and to a tool and a composition forming part of the kit.

BACKGROUND ART

Many ailments of the gastrointestinal system in humans are caused at least in part by bacteria. Such bacteria include those of the genus *Campylobacter*, and particularly *Helicobacter pylori*. For example, *Helicobacter pylori* can cause bacterial infections on the mucosal surface of the stomach. The chronic disorders of the stomach that is caused by *Helicobacter pylori* include peptic ulcers, gastritis, and cancer. It has further become well-known that *Helicobacter pylori* produce the urease enzyme in large amounts.

Thus, once a patient is showing symptoms of a stomach disorder, several tests can be used to diagnose for the presence of *Helicobacter pylori*. One such test that has gained widespread popularity is the rapid urease test, also known as the CLO test (*Campylobacter*-like organism test).

The CLO test is based on the ability of urease enzyme to convert urea into ammonia and carbon dioxide. Consequently, the CLO test includes the steps of contacting a stomach tissue sample with a gel composition that contains urea and a pH indicator that changes colour when there is a rise in pH. Phenol red is often used as a suitable indicator as it undergoes a conspicuous yellow to red colour change. If urease is present within the gastric material, urea will be broken down into ammonia to raise the pH and ultimately causes the pH indicator to change colour.

Although the CLO test has provided great advancements in the early detection of gastrointestinal disorders, the urea and other reagents contained within the gel composition have a tendency to degrade over time. Consequently, once formulated, the gel composition has a relatively short shelf life.

In order to increase the shelf-life of the CLO test kits, it is refrigerated to slow down the composition's degradation. In fact, many countries stipulate that the CLO test kits must be refrigerated to below 10° C. before permitting international transportation. Such refrigeration requires large refrigeration units that increase storage costs, both in capital costs to purchase the units, and in running and maintenance costs. Because of this, many developing countries cannot afford such CLO test kits. In addition, many remote hospitals do not have a reliable electricity supply to power the refrigeration near to an endoscopy room. For this reason a dedicated power generator is required to power the refrigerators, leading to additional costs being incurred. Alternatively, the refrigerators have to be centrally located in the hospital being remote from the endoscopy room, which is inconvenient as it delays the diagnosis of the patient by increasing the time required to fetch a CLO test kit and required an additional nurse to do the fetching legwork.

In view of the above, the need exists for a CLO test kit that has an improved shelf life.

Furthermore, urease testing normally forms only part of a diagnosis of a patient suffering from a gastrointestinal disorder. In most cases, an additional bacterial culture for DNA testing can greatly improve the diagnosis. Unfortunately the current CLO test kit described above does not preserve the bacterial sample. For this reason, once the CLO test is used, the CLO test kit containing the bacterial sample is simply discarded. For patients who failed eradication treatment, an additional endoscopy examination will be required to obtain a further tissue sample for bacterial culture and DNA testing. Clearly this may be problematic as the patient would have to make another appointment to see the specialist. This not only increases the workload of the specialist and nurses, but also delays and extends the patient treatment time, which leads to increased numbers of patients waiting for an endoscopy examination.

There is therefore a further need to be able to preserve the bacterial sample.

The above described background art is not intended to limit the application of the kit as disclosed herein.

SUMMARY OF THE INVENTION

According to one aspect of the present invention, there is provided a kit for the detection of urease, the kit comprising:
  a composition containing an indicator;
  a delivery tool arranged to deliver a tissue sample into contact with the composition; and
  urea carried on the delivery tool, whereby the urea is arranged to be delivered to the composition together with the tissue sample.

The composition may comprise a gel.

The composition may have a pH of less than 6.8.

The composition may comprise a buffer.

The composition may comprise a preservative arranged to preserve a tissue sample delivered into the composition.

The preservative may be phenol.

The indicator may be phenol red.

The delivery tool may comprise a holding part and a sampling part.

The delivery tool may comprise a frangible connection enabling the sampling part to be separated from the holding part.

The holding part may comprise an elongated stem being arranged to form a pointed end after separation of the sampling part.

The frangible connection may comprise an indentation in the stem.

The indentation may be a groove, notch or recess.

The indentation may surround the stem.

The sampling part may comprise one or more projecting members extending away from the holding part.

The projecting members may extend axially away from the holding part.

The projecting members may be brittle.

The projecting members may comprise one or more prongs.

The projecting members may be arranged to define a catchment area for receiving the tissue sample.

The projecting members may comprise a number of bristles arranged in a brush structure.

The urea may be provided on the projecting members.

The urea may be provided as a powder coating on the delivery tool.

The urea may be provided as a deposit obtained from a liquid solution applied to the delivery tool.

The urea may be provided as an integrally formed part of the delivery tool.

The urea may be sufficient to result in an effective concentration of about 20 mg urea per ml of composition during use after the urea has been delivered to the composition.

The urea may comprise 0.1 to 100 mg.

The urea may comprise 5 to 20 mg.

The composition may be contained in a well formed in a container.

The well may be arranged to contain 0.3 ml of the composition.

The container may comprise an interference protrusion being arranged to engage the delivery tool.

The interference protrusion may be provided on a base of the container so that the interference protrusion extends into the well.

The interference protrusion may be arranged to engage the delivery tool to assist delivering the tissue sample into the composition.

The container may comprise a chamber arranged to hold the delivery tool prior to use.

The container may comprise a tray having at least three discrete wells therein.

Two of the wells may contain the composition and a third well may contain a supply of urea.

The container may comprise a label being removably attached to the tray to resealably cover all the wells.

The label may be arranged to selectively be removed to open either one of the wells containing the composition or to open together the other wells.

The label may comprise a secure attachment to the tray being arranged to prevent the label from being removed and simultaneously opening all the wells.

The secure attachment may comprise a weld joint between the label and the tray.

The tray may comprise a magnifying lens associated with one of the wells.

According to another aspect of the present invention, there is provided a delivery tool for use with a composition in the detection of urease, the delivery tool comprising:

a holding part;

a sampling part; and a frangible connection between the holding part and the sampling part enabling the sampling part to be separated from the holding part during use.

According to another aspect of the present invention, there is provided a composition for use in the detection of urease, the composition comprising:

a gel;

an indicator provided in the gel; and a preservative provided in the gel and being arranged to preserve a tissue sample delivered into the gel.

BRIEF DESCRIPTION OF DRAWINGS

The present invention will now be described, by way of example, with reference to the accompanying schematic drawings, in which:

FIG. 8 is a perspective view of the kit of FIG. 7 shown in use in a first configuration; and FIG. 9 is an alternate perspective view of the kit of FIG. 7 shown in use in a second configuration.

DETAILED DESCRIPTION OF THE DRAWINGS

Referring to FIGS. 1 to 6, there is shown a first embodiment of a kit 10 for the detection of urease. The kit 10 comprises a delivery tool 12 for bringing a gastric biopsy tissue sample into contact with a composition 14 supplied in a container 40.

Figure 2:
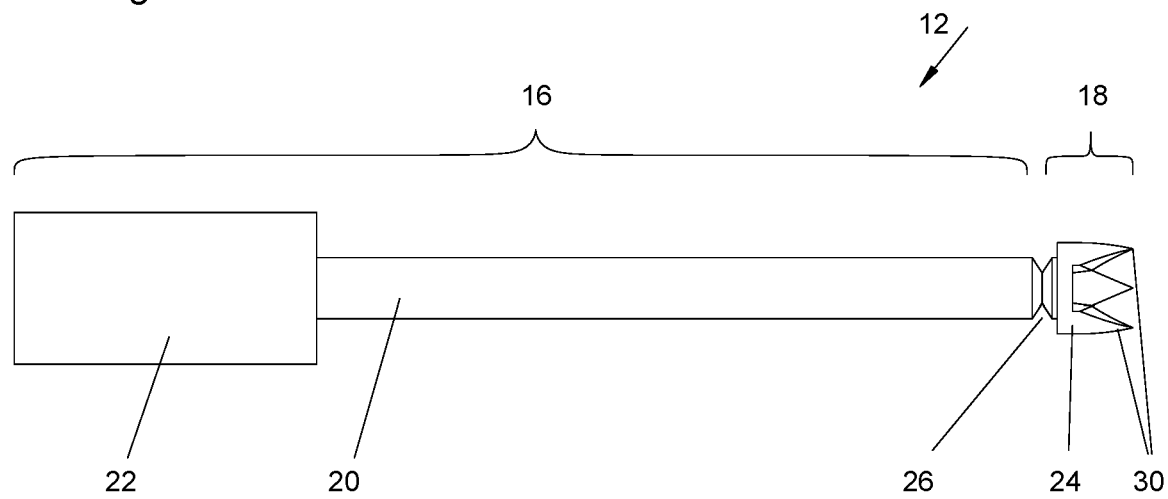
FIG. 2 is an enlarged side view of the delivery tool shown in FIG. 1.

The delivery tool 12 is shown in greater detail in FIG. 2 and comprises a holding part 16 and a sampling part 18. The holding part 16 is in the form of an elongated cylindrical stem 20 having a handle 22 at one end. The handle 22 has the shape of an enlarged flat rectangular blade, extending both axially and radially outward from the stem 20, and is adapted for enabling a person to easily grip and manipulate the delivery tool 12. It will be appreciated that the handle 22 can have any other suitable shape or size and should merely be able to be relatively comfortably gripped by the person. As such, the handle 22 could be disc-shaped, having a flat round appearance, or could have any other shape that is commonly associated with implements for being gripped by a person's fingers. Alternatively the handle 22 could be entirely omitted, such that the delivery tool 12 resembles a toothpick; provided that the stem 20 is sufficiently long and thick enabling it to be comfortably gripped. In the exemplary embodiment, the stem 20 has a diameter of about 3 mm while the holding part 16 has a length of about 50-80 mm.

The sampling part 18 is provided at an end of the stem 20 opposed to the handle 22. The sampling part 18 is arranged to be used to collect a tissue sample and to insert the tissue sample into the composition 14. The sampling part 18 comprises a deposit of urea thereon so that, in use, the urea is delivered to the composition 14 together with the tissue sample.

Figure 1:
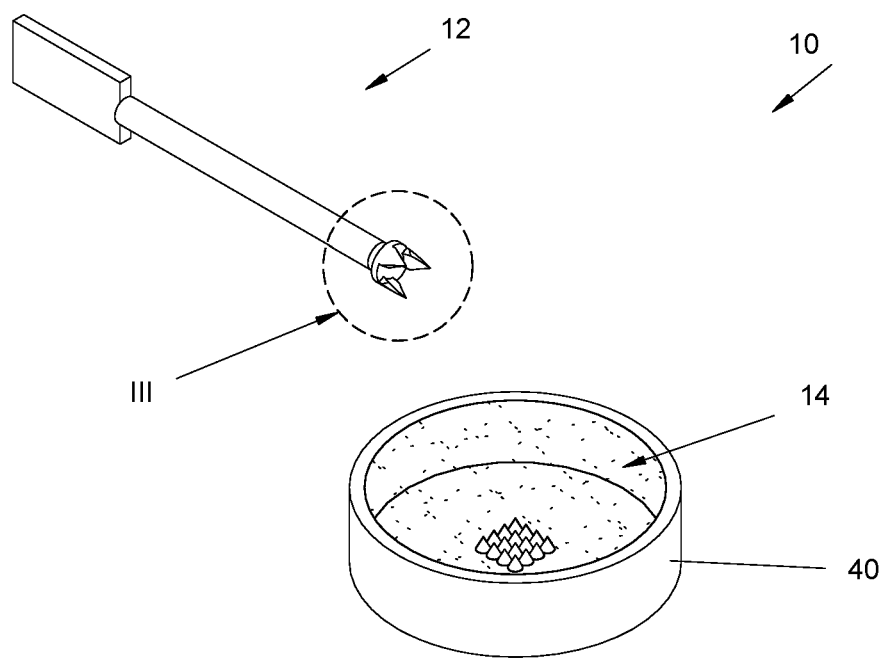
FIG. 1 is a perspective view of a first embodiment of a kit for the detection of urease, the kit comprising a delivery tool and a container filled with a composition.
Figure 3:
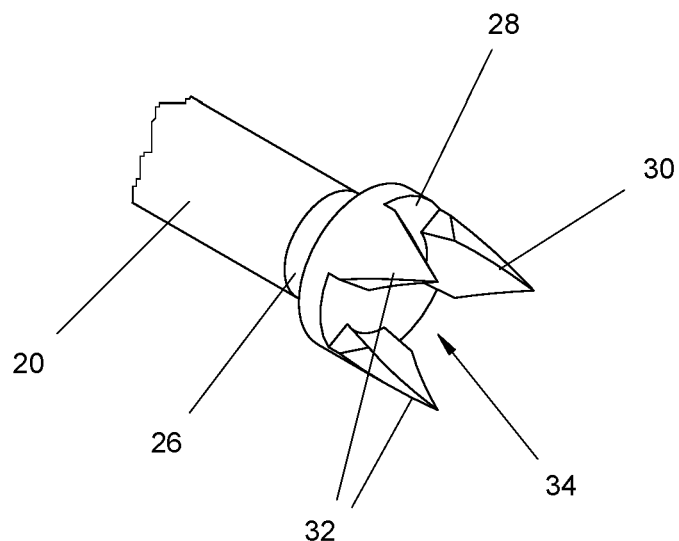
FIG. 3 is an enlarged perspective view of the area indicated by arrow III in FIG. 1, showing a sampling part of the delivery tool.

In one embodiment, shown in FIGS. 1-3, the sampling part 18 comprises a head 24 that is integrally formed with the stem 20. A neck 26 is provided between the head 24 and the stem 20, which neck 26 defines a frangible connection permitting the head 24 to be separated from the stem 20 during use. The neck 26 comprises an annular constriction of stem 20 reducing its diameter to about 1-2 mm. However, it is envisaged that in other embodiments the neck 26 can be formed by a simply indentation, such as a groove, notch or recess cut partway into the stem 20.

The head 24 has the appearance of a crown comprising a base 28 that is arranged transversal to the stem 20 with a number of projections 30 extending axially away from the base 28 distal to the stem 20. The base 28 is disc-shaped and the projections 30 are in the form of tapered prongs 32 that are circumferentially spaced around a perimeter of the base 28. Although only three prongs 32 are shown, additional prongs can be provided. Alternatively, it will be appreciated that the base 28 can be provided in other shapes, such as being polygonal, wherein one or more prongs 32 can be provided along each of the sides of the polygon. Similarly, the prongs 32 can comprise any pointed shape, such as conical. Together the base 28 and prongs 32 define a partially enclosed catchment area 34 arranged to receive and hold the tissue sample during use. In the exemplary embodiment the prongs 32 have a length of about 2.5 mm.

In another embodiment, the base 28 can be planar so that the prongs 32 are aligned along a common plane, thus causing the head 24 to have the appearance of a fork. In such case the tissue sample can be held either by the prongs 32 piercing the tissue sample or by wedging the tissue sample between the prongs 32 so that it is frictionally held in interstitial spaces between the prongs 32.

Figure 4:
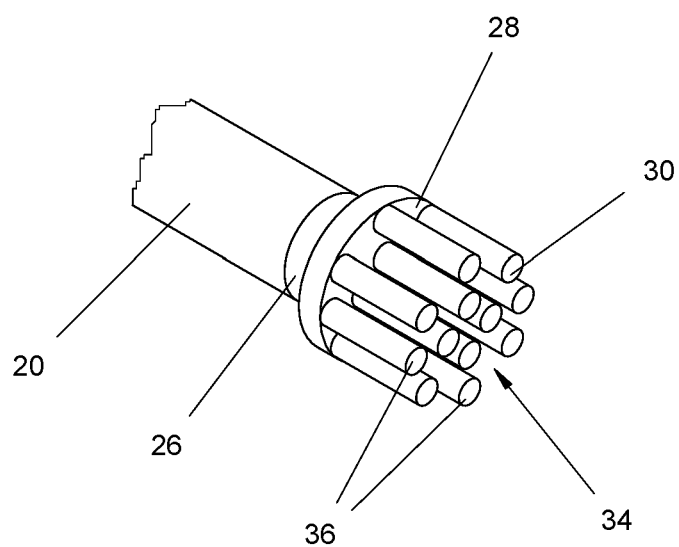
FIG. 4 is an alternative embodiment of the sampling part of the delivery tool.

In yet another embodiment, shown in FIG. 4, the sampling part 18 is in the form of a brush comprising a number of bristles 36 extending from the base 28 that is integrally formed with the stem 20. In one adaptation of this embodiment, the bristles 36 can extend axially directly from the stem 20, e.g. being squid-like in appearance. In yet a further adaptation of this embodiment, the bristles 36 can extend radially or spherically from the stem 20, e.g. being similar in appearance to a pincushion. In each of these embodiments the bristles 36 will also have a length of about 2.5 mm. The bristles are relatively rigid so that, in use, the soft tissue sample can be pierced by the bristles 36 and held in interstitial spaces between the bristles 36.

In the above embodiments, the urea is provided on the base 28 and on the prongs 32 (or the bristles 36). The urea can be provided as a powder coating using urea powder. Alternatively, the urea can be provided as a liquid coating by immersing the base 28 and prongs 32 into a urea solution and allowing the liquid coating to dry. Yet further, the urea can be provided by integrally forming the entire head 24, or at least the prongs 32, from urea.

The sampling part 18 contains urea in the amount of about 0.1-100 mg, preferably about 5-20 mg.

Figure 5:
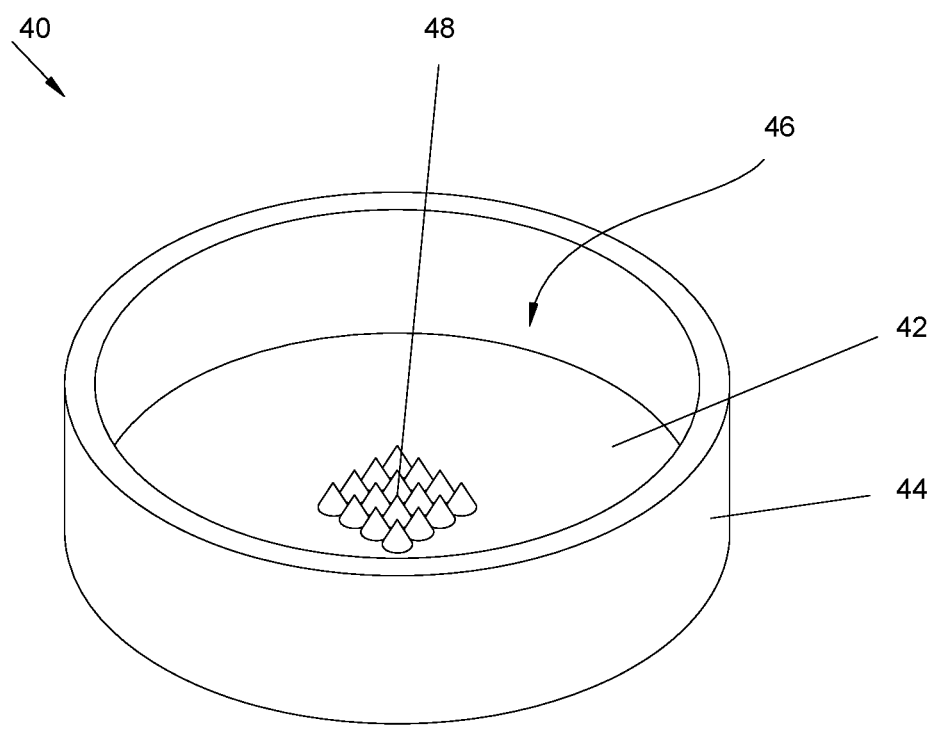
FIG. 5 is an enlarged perspective view of the container shown in FIG. 1.

The composition 14 is contained in the container 40, which is shown in greater detail in FIG. 5. The container 40 comprises a container base 42 from which cylindrical sidewalls 44 extend so as to define a well 46 in which the composition 14 is contained. In the exemplary embodiment the well 46 is about 8 mm deep and contains about 0.3 ml of the composition 14. Although not shown in the drawings, the container 40 can comprise a removable cover, such as a plastic film, for hermetically sealing the well 46 to prevent contamination of the composition 14 prior to use.

The container 40 optionally includes interference protrusions 48 that extend into the well 46. The protrusions 48 can be any form of buttress being adapted to engage with the prongs 32 or with the bristles 36. As such the protrusions 48 can extend from the base 42 or from the sidewalls 44. In the exemplary embodiment, the protrusions 48 are a plurality of conical structures extending from the base 42.

The composition 14 comprises wet reagents provided in a water-based gel form that contains a pH indicator. The pH indicator is selected to be suitable for testing for ammonia that will be formed during use of the kit 10 when urea is broken down by the urease enzyme. Although there are many such suitable indicators, phenol red is commonly used in urease testing kits. For this reason, the exemplary embodiment of the composition comprises phenol red as the pH indicator. Phenol red undergoes a colour change from yellow (indicating an acidic state) to red (indicating a basic state) at about a pH of 6.9. Accordingly, the composition 14 is buffered to maintain a pH value of below 6.8, so that any rise in pH due to the formation of ammonia causes the indicator to undergo a colour change from yellow to red.

The composition 14 further includes a preservative in an effective concentration to preserve the tissue sample when inserted into the well 46 and immersed within the composition 14. In the present embodiment the preservative is phenol.

Figure 6:
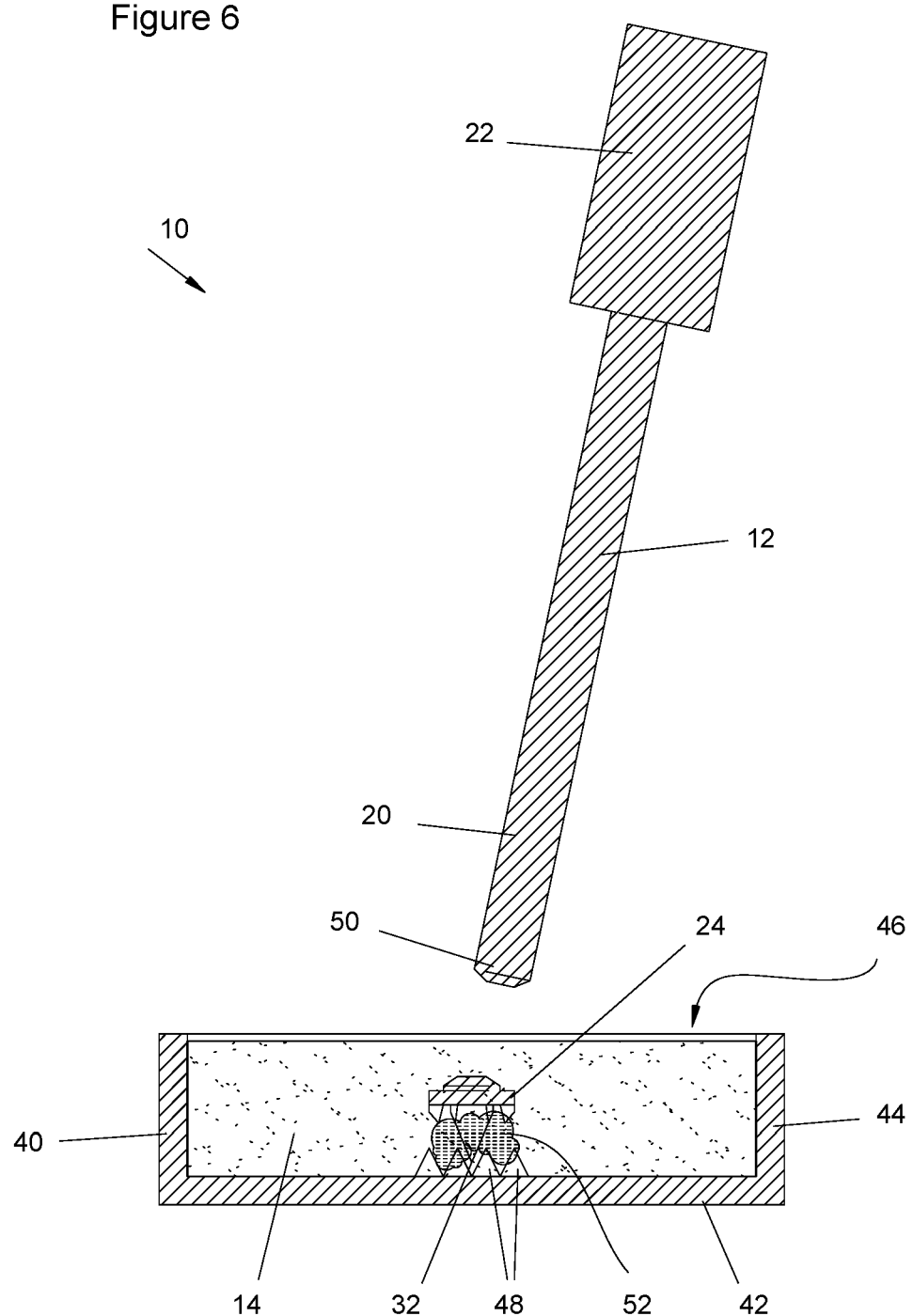
FIG. 6 is a sectional side view of the kit of FIGS. 1 to 5 shown during use.

The use of the kit 10 to detect the presence of urease in the tissue sample will now be described with reference to FIG. 6.

A tissue sample 52 is obtained by gastric biopsy and removed from the biopsy forceps by passing the sampling part 18 of the delivery tool 12 through the tissue sample so that at least some of the tissue sample 52 is captured on the sampling part 18. As the tissue sample inherently contains some moisture, the dry urea powder coating the prongs 32 or bristles 36 will start to dissolve. The tissue sample 52 is subsequently delivered into contact with and immersed within the composition 14. As the sampling part 18 is inserted into the composition 14, the wet reagents in the gel of the composition 14 dissolve any remaining urea powder on the prongs 32.

It will be appreciated that before the delivery tool 12 is contacted with the tissue sample 52 or inserted into the composition 14, the urea coating on the prongs 32 is kept dry. The urea is only delivered to the composition 14 together with the tissue sample, but is kept separated therefrom prior to use.

The amount of urea powder provided on the delivery tool 12 is predetermined, so that when the urea dissolves or is mixed into the composition 14, the effective concentration of urea within the composition 14 is about 20 mg per millilitre. At this concentration there is sufficient urea to cause a sufficiently visible colour change of the phenol red indicator.

By maintaining the urea in a powdered form separate from the composition 14 prior to use, the urea remains more stable. Further, by maintaining the urea separate from the composition 14, the handling requirements of the kit 10 become more relaxed. For instance, by maintaining the urea separate from the composition 14, there is no need to refrigerate either the delivery tool or the composition 14 prior to use, such as during storage or shipping. Also the process conditions for manufacturing the composition 14 become more relaxed because of its improved stability.

When inserting the sampling part 18 into the well 46, the prongs 32 and/or bristles 36 are contacted against the sidewalls 44 or base 42 of the container 40 to break them off inside the well 46 causing the tissue sample to remain immersed in the composition 14. Thus in the embodiment of the delivery tool 12 shown in FIG. 4, the bristles 36—being relatively thin—can be broken off rather easily by simply pressing them against the base 42. The bristles 36 can be made of a relatively brittle material, wherein the bristles will be sufficiently resilient not to break when scraping them through the tissue sample to capture the tissue sample, but being sufficiently brittle so that they do break off when pressed against the base 42.

Similarly, if sufficient force can be applied to the embodiment of the delivery tool 12 shown in FIG. 3, also the prongs 32 can be broken off. However, as the prongs 32 are sturdier, it is expected that they will not break as easily. For this reason the prongs 32 can be manoeuvred to engage with the interference protrusions 48 and twisted thereagainst so that the head 24 snaps off the stem 20 at the neck 26. A pointed end 50 remains on the stem 20 that can be used to obtain a further tissue sample for conducting a second test, or the pointed end 50 can be used to scrape clean the biopsy forceps.

It is envisaged that the delivery tool 12 will be made of plastic or wood so that the head 24 can be relatively easily snapped off during use.

In respect of the embodiment wherein the head 24 is integrally made of urea, it will not be necessary to snap off the head 24. Instead the entire head 24 can be allowed to dissolve in the composition 14 so that the stem 20 can be removed leaving the tissue sample 52 behind in the composition 14.

Subsequently the tissue sample 52 remains in the composition 14 and is preserved by the phenol, allowing the container 40 to be sealed, e.g. resealed with its cover, and dispatched to a testing lab for further testing to be done on the tissue sample 52.

Figure 7:
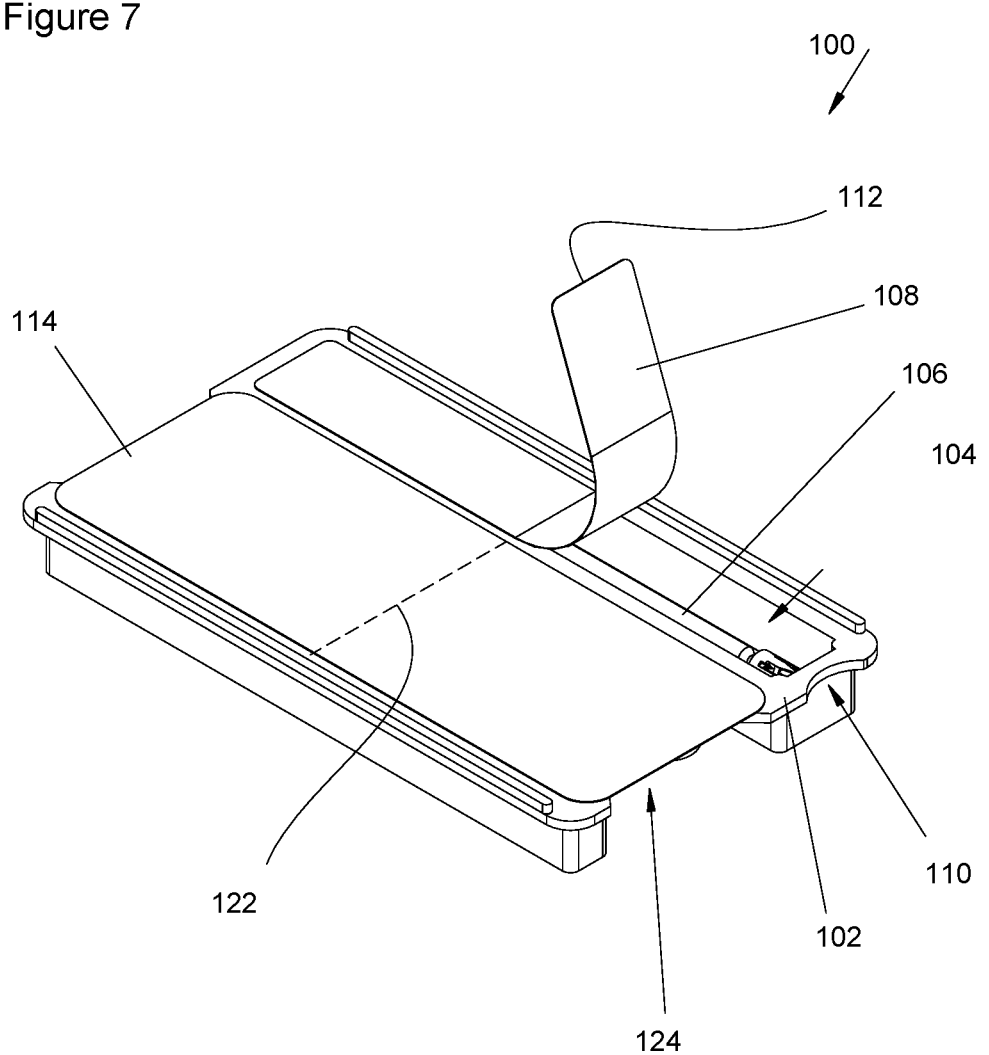
FIG. 7 is a perspective view of a second embodiment of a kit for the detection of urease.

Referring now to FIGS. 7 to 9, there is shown a second embodiment of a kit 100 for the detection of urease.

The kit 100 comprises a tray 102 in which an elongated chamber 104 is provided being suitably sized to contain a delivery tool 106. The delivery tool 106 has a similar structure to the delivery tool 12 and therefore the respective parts of the delivery tool 106 are indicated using the same reference numerals as used in relation to the delivery tool 12. However, the delivery tool 106 is a sterile tool and does not contain and is not provided with any urea on its sampling part 18.

The chamber 104 is sealed by a removable cover 108 so that the delivery tool 106 is initially kept in a sterile environment within the chamber 104. However, if needed, the delivery tool 106 can be enclosed within a hermitically sealed sachet within the chamber 104. A finger recess 110 is provided in one end of the tray 102 adjacent to the chamber 104. The recess 110 extends beneath an edge 112 of the cover 108 so that in use the edge 112 can be easily gripped by a person's finger to pull the cover 108 loose from the tray 102 so as to enable the delivery tool 106 to be removed from the chamber 104. More than one delivery tool 106 may be provided in the chamber 104.

A label 114 is attached to the tray 102 so as to seal a number of wells provided in the tray 102. The wells comprise a first test well 116 located towards one end of the tray 102, a second test well 118 located towards an opposed end of the tray 102, and a supply well 120 located in the vicinity of the second test well 118. The first and second test wells 116, 118 are similar to the well 46 in that they each contain a volume of the composition 14, i.e. comprising the wet reagents including a gel, pH indicator and preservative. Similarly, although not shown in FIGS. 7-9, the first and second test wells 116, 118 are also provided with protrusions being equivalent to the protrusions 48 shown in FIGS. 5 and 6. In contrast, the supply well 120 contains a supply of urea and does not have any protrusions therein.

It will be appreciate that in other embodiments, the cover 108 and the label 114 can be integrally formed as a single item.

The label 114 is resealably attached to the tray 102 and as such the label 114 has a suitable adhesive coating to enable it to be detached from and reattached to the tray 102. The adhesive should permit the label 114 to be fully reattached at least once, preferably more than once. The label 114 is substantially rectangular in shape and is arranged so that it can be selectively peeled away from the tray 102 from opposed ends thereof. FIG. 8 shows the label 114 being peeled away from the tray 102 so as to open and permit access to the first test well 116, whereas FIG. 9 shows the label 114 being peeled away from the tray 102 so as to open and permit access to both the second test well 118 and the supply well 120.

In one embodiment, it is envisaged that the label 114 will be securely attached to the tray 102 along a centre part thereof (indicated by dashed line 122 in FIG. 7). This will prevent the label 114 from being inadvertently peeled away too far or being fully removed from the tray 102, whereby both the first and second wells 116, 118 are simultaneously opened. Such a secure attachment could be achieved by welding the label 114 to the tray 102 in the vicinity of the line 122, e.g. by heat welding or ultrasonic welding. Alternatively, fold-over tabs can extend outwardly from the label 114 in the vicinity of the line 122 for being folded over and adhered to the tray 102.

Finger recesses 124 are provided in opposed ends of the tray 102 to extend beneath the opposed edges 126, 128 of the label 114. Thus in use either edge 126, 128 of the label 114 can be easily gripped to temporarily lift the associated part of the label 114 away from the tray 102, as shown in FIGS. 8 and 9, whereafter the label 114 can be reattached to the tray 102 to reseal the first or second wells 116, 118.

In the exemplary embodiment the label 114 is coloured white or at least has a white coloured lower face being attached to the tray 102. Also the tray 102 is made of a transparent material so that the lower face of the label 114 can be seen through the tray 102. Thereby label 114 provides a white background against which the colour of the composition 14 in the first and second wells 116, 118 can be easily seen and any colour change of the indicator in the composition 14 during use can be discerned relatively easily.

In use, after removing the delivery tool 106 from the chamber 104, a tissue sample is captured on the sampling part 18. That tissue sample can be selectively deposited into either the first or second test well 116, 118 after lifting the relevant part of the label 114 and subsequently reattaching the label 114 to the tray 102 to close the wells 116, 118.

In most cases, it is envisaged that separate tissue samples will be placed into each of the first and second test wells 116, 118. Thus initially a first tissue sample will be deposited into the first test well 116. This is achieved by capturing the first tissue sample on the sampling part 18 and then breaking off the sampling part 18 of the delivery tool 106 in the first test well 116. Before capturing a second tissue sample, the remaining pointed end 50 of the delivery tool 106 is first dipped into the urea contained in the supply well 120 so that the urea is deposited together with the second tissue sample into the second test well 118. Clearly it will be understood that if more than one delivery tool 106 is provided in the chamber 104, then also the second tissue sample (with urea) can be delivered into the second test well 118 by breaking off its sampling head 18 therein. By providing the separate tissue samples in each of the first and second test wells 116, 118, the first tissue sample can be preserved in a sterile environment for later testing if needed, e.g. DNA testing, whereas the second tissue sample can provide an immediate result of a urease test.

The above order of depositing tissue samples is viewed as being preferable to avoid the possibility of urea entering the first test well 116, which could lead to a shorter period of preservation of the first tissue sample. In this regard it will be appreciated that with careful use, it may be possible to reverse the depositing order by only partially dipping the sampling part 18 into the urea and then breaking off the sampling part 18 with the first tissue sample in the second test well 118, whereafter the pointed end 50 is used to deposit the second tissue sample into the first test well 116. However, this does carry risk that some urea may inadvertently be deposited into the first test well 116. It will further be appreciated that if more than one delivery tool 106 is provided, then separate delivery tools can be used to deposit each of the first and second tissue samples and, in such case, the order of depositing is not important.

The initial urease test is conducted by inspection of the reaction between the tissue sample and the urea within the second test well 118. Subsequently the tray 102 can be dispatched to a testing laboratory where the label 114 can be repeatedly detached and reattached to the tray 102 to permit a part of the tissue sample in the first test well 116 to be removed. This could occur on multiple occasions, such as to conduct different tests on the tissue sample or to conduct the test in various laboratories.

In some cases when the kit 100 remains unused and is stored for a lengthy period, the composition 14 in the test wells 116, 118 may age and slowly change colour. For instance, fresh composition 14 may have a relatively light yellowish colour that becomes progressively darker as it ages to be more honey coloured. This darker colour can occasionally hinder the visual inspection of the second test well 118 when conducting the urease test as it is not always easy to discern the colour change from the darker yellow to red. The kit 100 has the advantage in partially alleviating this difficulty because the composition 14 in each of the first and second test wells 116, 118 should age at the same rate. Accordingly the composition 14 in the first test well 116 can be used as a control, against which any colour change in the composition 14 in the second test well 118 during a urease test can be compared. This assists in identifying any small colour changes.

In yet a further embodiment not shown in the drawings, it is envisaged that the bottom part of the second test well 118 can be convexly curved so as to form a type of magnifying glass to provide a visual magnifying effect when looked through. This would assist in discerning any colour change in the composition 14 during a urease test. The convex curve could be provided to curve outwardly away from or inwardly into the second test well 118.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

For example, although the label 114 is shown being lifted from opposed ends of the tray 102 with the test wells 116, 118 being substantially centrally aligned in the tray 102, it would be possible to rearrange the wells so that they are diagonally aligned across the tray 102 whereby the label 114 would be arranged to be lifted from diagonally opposing corners of the tray 102. Further, instead of welding the label 114 to the tray 102, it would be possible to provide central wings on the label 114 that could be folded around the tray 102 to prevent the label 114 from being opened to too great an extent.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A kit for the detection of urease, the kit comprising:
   a composition containing an indicator, wherein the composition is contained in one or more wells formed in a container;
   a delivery tool arranged to deliver a tissue sample into contact with the composition, wherein the delivery tool comprises a holding part and a sampling part,
      wherein the sampling part is configured to collect a tissue sample and deliver the tissue sample into the composition in the one or more wells, and
      wherein the holding part and the sampling part are separated by a frangible connection that enables the sampling part to be separated from the holding part upon engagement of the sampling part with a sidewall or base of the container forming the one or more wells; and
   urea carried on the sampling part of the delivery tool, whereby the urea is carried in a manner such that at least a portion of the urea is dissolved by the tissue sample when the tissue sample is collected on the sampling part, and the sampling part and the tissue sample are both delivered into contact with and immersed within the composition within the one or more wells.

2. The kit of claim 1, wherein the container comprises a tray, the tray having a sealed chamber sized to contain the delivery tool prior to use.

3. The kit of claim 2, wherein the one or more wells comprise two wells formed in the tray which contains the composition.

4. The kit of claim 3, comprising a resealably attached label for selectively covering and uncovering the wells.

5. The kit of claim 4, wherein the label is securely attached to the tray at a location between the two wells to prevent the label from being fully removed from the tray and enabling respective portions of the label to be peeled from the tray up to the location to provide access to or close the wells independently of each other.

6. The kit of claim 4, wherein the tray comprises a magnifying lens associated with one of the wells.

7. The kit of claim 2, wherein the tray is made of a transparent material wherein a lower face of the label can be seen through the tray.

8. The kit of claim 7, wherein the lower face of the label is coloured white.

9. The kit of claim 2, wherein the tray comprises a supply well containing a supply of urea.

10. The kit of claim 2, wherein the urea is carried on the delivery tool when contained in the sealed chamber.

11. The kit of claim 1, wherein the holding part comprises an elongated stem being arranged to form a pointed end after separation of the sampling part.

12. The kit of claim 1, wherein the sampling part comprises one or more projecting members extending away from the holding part.

13. The kit of claim 12, wherein the projecting members extend axially away from the holding part.

14. The kit of claim 12, wherein the projecting members comprise one or more prongs.

15. The kit of claim 12, wherein the projecting members are arranged to define a catchment area for receiving the tissue sample.

16. The kit of claim 12, wherein the projecting members comprise a number of bristles arranged in a brush structure.

17. The kit of claim 12, wherein the urea is provided on the projecting members.

18. The kit of claim 1, wherein the urea is provided as a powder coating on the delivery tool.

19. The kit of claim 1, wherein the urea is provided as a deposit obtained from a liquid solution applied to the delivery tool.

20. The kit of claim 1, wherein after separation from the holding part, the sampling part further comprises a pointed end.

21. The kit of claim 19, wherein the pointed end is configured to obtain and deliver a second tissue sample into contact with the composition.

22. The kit of claim 1, wherein the base or sidewall of at least one of the one or more wells comprises interference protrusions.

23. The kit of claim 22, wherein the interference protrusions comprise a plurality of conical structures.

* * * * *